United States Patent
Morita

(10) Patent No.: US 10,054,783 B2
(45) Date of Patent: Aug. 21, 2018

(54) ENDOSCOPE OBJECTIVE OPTICAL SYSTEM

(71) Applicant: OLYMPUS CORPORATION, Hachioji-shi, Tokyo (JP)

(72) Inventor: Kazuo Morita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 11 days.

(21) Appl. No.: 15/666,532

(22) Filed: Aug. 1, 2017

(65) Prior Publication Data

US 2017/0329124 A1 Nov. 16, 2017

Related U.S. Application Data

(63) Continuation of application No. PCT/JP2016/061368, filed on Apr. 7, 2016.

(30) Foreign Application Priority Data

Apr. 9, 2015 (JP) .................................. 2015-079789

(51) Int. Cl.
*G02B 23/02* (2006.01)
*A61B 1/00* (2006.01)
(Continued)

(52) U.S. Cl.
CPC .......... *G02B 23/02* (2013.01); *A61B 1/00096* (2013.01); *A61B 1/00183* (2013.01); *G02B 17/08* (2013.01); *G02B 23/243* (2013.01)

(58) Field of Classification Search
CPC ...... G02B 23/02; G02B 23/243; G02B 17/08; A61B 1/00096; A61B 1/00183
(Continued)

(56) References Cited

U.S. PATENT DOCUMENTS

| | | | |
|---|---|---|---|
| 3,880,148 A | 4/1975 | Kanehira et al. | |
| 3,994,557 A | 11/1976 | Hopkins | |

(Continued)

FOREIGN PATENT DOCUMENTS

| | | | |
|---|---|---|---|
| JP | 49053847 A | 5/1974 | |
| JP | 50141347 A | 11/1975 | |

(Continued)

OTHER PUBLICATIONS

International Search Report (ISR) and Written Opinion dated Jul. 5, 2016 issued in International Application No. PCT/JP2016/061368.

(Continued)

*Primary Examiner* — Jack Dinh
(74) *Attorney, Agent, or Firm* — Holtz, Holtz & Volek PC

(57) ABSTRACT

An endoscope objective optical system includes an optical-path deflecting prism group and a lens group. A visual-field direction of the endoscope objective optical system is variable by moving a prism in the optical-path deflecting prism group. The optical-path deflecting prism group includes, in order from an object side, a first prism, a second prism, and a third prism, which are disposed to be in mutual proximity. The visual-field direction is variable to a first direction by the first prism undergoing a rotational movement with respect to the second prism, and the visual-field direction is variable to a second direction which differs from the first direction, by the first prism and the second prism undergoing rotational movement integrally with respect to the third prism.

3 Claims, 16 Drawing Sheets

(51) Int. Cl.
 *G02B 23/24* (2006.01)
 *G02B 17/08* (2006.01)
(58) Field of Classification Search
 USPC .......................................................... 359/733
 See application file for complete search history.

(56) References Cited

U.S. PATENT DOCUMENTS

| | | |
|---|---|---|
| 8,684,915 B2 | 4/2014 | Katakura |
| 2006/0252995 A1 | 11/2006 | Hoeg et al. |
| 2006/0256450 A1 | 11/2006 | Tesar et al. |
| 2011/0286112 A1 | 11/2011 | Orihara et al. |
| 2013/0085338 A1 | 4/2013 | Buerk |
| 2013/0242071 A1 | 9/2013 | Wada et al. |

FOREIGN PATENT DOCUMENTS

| | | | |
|---|---|---|---|
| JP | 63262613 A | 10/1988 | |
| JP | 09061722 A | 3/1997 | |
| JP | 2006201796 A | 8/2006 | |
| JP | 2006204924 A | 8/2006 | |
| JP | 2013215560 A | 10/2013 | |
| WO | 2011027622 A1 | 3/2011 | |
| WO | 2012081349 A1 | 6/2012 | |

OTHER PUBLICATIONS

International Preliminary Report on Patentability (IPRP) dated Oct. 19, 2017 issued in counterpart International Application No. PCT/JP2015/061368.

ENDOSCOPE OBJECTIVE OPTICAL SYSTEM

CROSS-REFERENCE TO RELATED APPLICATION

The present application is a continuation application of PCT/JP2016/061368 filed on Apr. 7, 2016 which is based upon and claims the benefit of priority from Japanese Patent Application No. 2015-079789 filed on Apr. 9, 2015; the entire contents of which are incorporated herein by reference.

BACKGROUND OF THE INVENTION

Field of the Invention

The present invention relates to an endoscope objective optical system.

Description of the Related Art

An endoscope is an apparatus that has been used widely in a medical field and an industrial field. Particularly, in the medical field, images of various sites inside a body cavity are achieved by an endoscope inserted into the body cavity. Diagnosis of a site observed is carried out by using these images. In such manner, endoscopes have been used for observation and diagnosis of various sites inside the body cavity.

In a case of changing a direction of observation while carrying out observation of inside of body cavity by an endoscope, a front-end side of an inserting portion of the endoscope is to be bent. Accordingly, it is possible to change an observation field of view vertically or in a leftward-rightward direction (refer to International Unexamined Patent Application Publication No. 2012/081349, Japanese Patent Application Laid-open Publication No. 2006-201796, and US Unexamined Patent Application Publication No. 2013:0085338).

SUMMARY OF THE INVENTION

An endoscope objective optical system according to the present invention includes an optical-path deflecting prism group, and a lens group, wherein a visual-field direction of the endoscope objective optical system is let to be variable by moving a prism in the optical-path deflecting prism group, and the optical-path deflecting prism group includes in order from an object side, three prisms namely, a first prism, a second prism, and a third prism, and the first prism, the second prism, and the third prism are disposed to be in mutual proximity, and the visual-field direction is let to be variable to a first direction by the first prism undergoing a rotational movement with respect to the second prism, and furthermore, the visual-field direction is let to be variable to a second direction which differs from the first direction, by the first prism and the second prism undergoing rotational movement integrally with respect to the third prism, wherein the endoscope objective optical system satisfies the following conditional expression (1)

$$0.9 \leq L/FL \leq 1.5 \quad (1)$$

where,

L denotes a total air conversion length (unit mm) of the first prism, the second prism, and the third prism in the optical-path deflecting prism group, and here the total air conversion length is a value obtained by summing up a value obtained by dividing a length of an optical axis passing through the first prism by a refractive index for a d-line nd1 of a glass material of the first prism, a value obtained by dividing a length of an optical axis passing through the second prism by a refractive index for the d-line nd2 of a glass material of the second prism, and a value obtained by dividing a length of an optical axis passing through the third prism by a refractive index for the d-line nd3 of a glass material of the third prism, and FL denotes a focal length (unit mm) of the endoscope objective optical system.

BRIEF DESCRIPTION OF THE DRAWINGS

FIG. 10 is still another perspective view showing an arrangement of the endoscope objective optical system according to the first embodiment;

DETAILED DESCRIPTION OF THE INVENTION

Figure 1A:
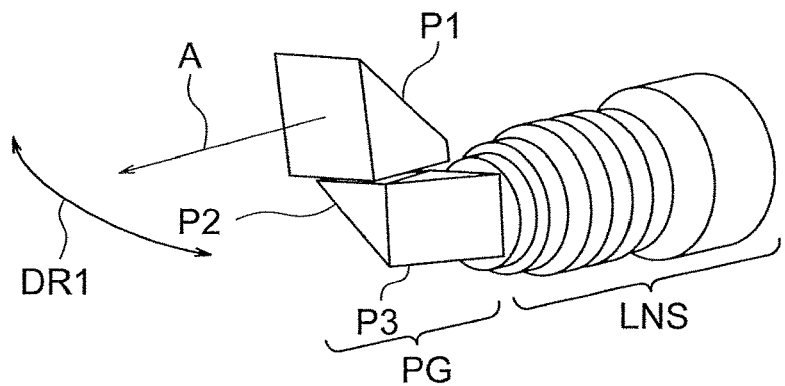
FIG. 1A is a perspective view showing an arrangement of an endoscope objective optical system according to a first embodiment.
Figure 1B:
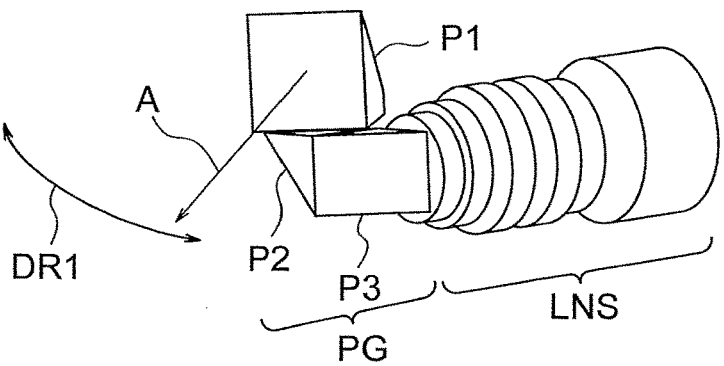
FIG. 1B is another perspective view showing an arrangement of the endoscope objective optical system according to the first embodiment.
Figure 1C:
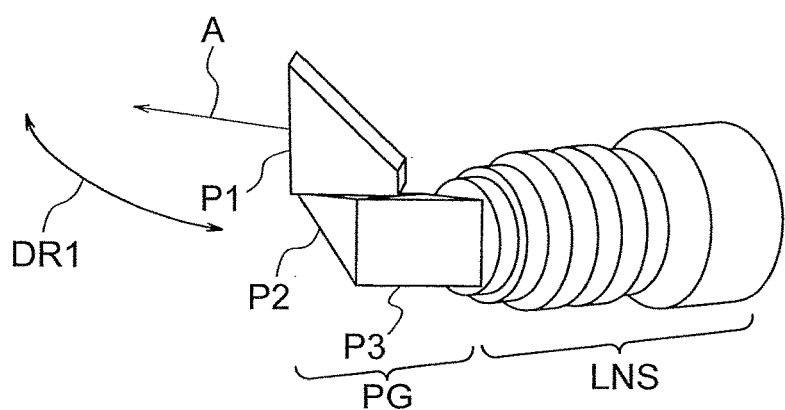
FIG. 1D is still another perspective view showing an arrangement of the endoscope objective optical system according to the first embodiment.
FIG. 1E is still another perspective view showing an arrangement of the endoscope objective optical system according to the first embodiment.
Figure 1D:
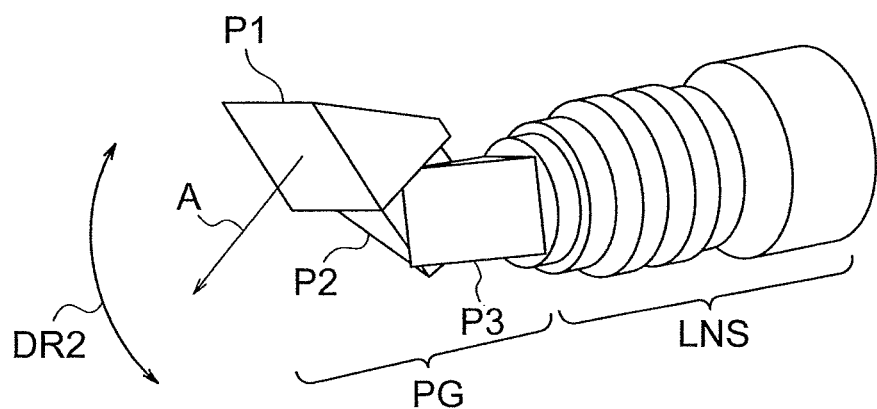
Figure 1E:
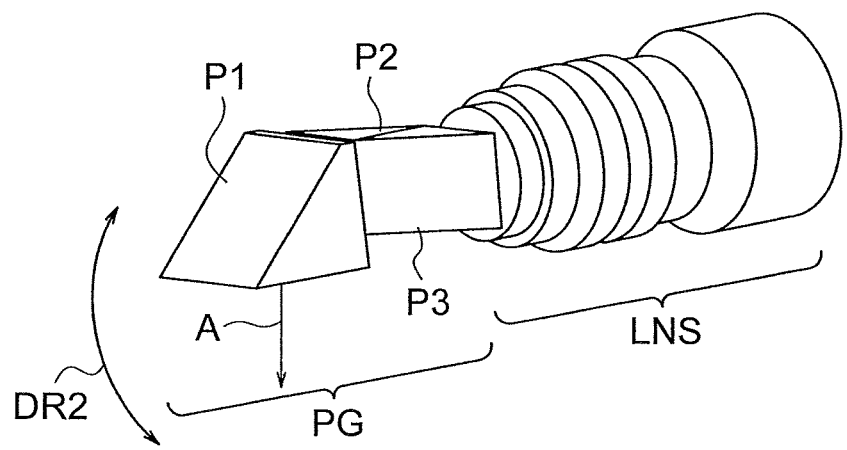

Reasons for and effects of adopting such arrangement for an endoscope objective optical system according to the present embodiment will be described below by using the accompanying diagrams. However, the present invention is not limited to the embodiments described below.

FIG. 1A, FIG. 1B, FIG. 1C, FIG. 1D, and FIG. 1E are diagrams showing a schematic arrangement of an endoscope objective optical system according to a first embodiment.

The endoscope objective optical system includes an optical-path deflecting prism group PG and a lens group LNS. A visual-field direction A is let to be variable by moving a prism in the optical-path deflecting prism group PG.

The optical-path deflecting prism group PG includes in order from an object side, three prisms namely, a first prism P1, a second prism P2, and a third prism P3. Each of the first prism P1, the second prism P2, and the third prism P3 is a right-angle prism. The first prism P1, the second prism P2, and the third prism P3 are disposed to be in mutual proximity. Moreover, the visual-field direction A is let to be variable to a first direction DP1 by the first prism P1 undergoing a rotational movement with respect to the second prism P2. Furthermore, the visual-field direction A is let to be variable to a second direction DR2 which differs from the first direction DR1, by the first prism P1 and the second prism P2 undergoing rotational movement integrally with respect to the third prism P3.

Accordingly, it is possible to change the field of view to an arbitrary direction without bending the endoscope, even in a narrow space. Moreover, it is preferable that the first direction DR1 and the second direction DR2 are orthogonal at 90 degrees.

Moreover, according to a preferable aspect of the present invention, it is preferable to satisfy the following conditional expression (1).

$$0.9 \leq L/FL \leq 1.5 \quad (1)$$

where,

L denotes a total air conversion length (unit mm) of the first prism, the second prism, and the third prism in the optical-path deflecting prism group, and here the total air conversion length is a value obtained by summing up a value obtained by dividing a length of an optical axis passing through the first prism P1 by a refractive index for a d-line nd1 of a glass material of the first prism P1, a value obtained by dividing a length of an optical axis passing through the second prism P2 by a refractive index for the d-line nd2 of a glass material of the second prism P2, and a value obtained by dividing a length of an optical axis passing through the third prism by a refractive index for the d-line nd3 of a glass material of the third prism P3, and FL denotes a focal length (unit mm) of the endoscope objective optical system.

Conditional expression (1) regulates an appropriate size of the optical-path deflecting prism group PG. By satisfying conditional expression (1), it is possible to make small the size of the optical-path deflecting prism group PG. Accordingly, it is possible to built-in the endoscope objective optical system in an inserting portion of an endoscope having a small diameter.

When a value falls below a lower limit value of conditional expression (1), a size of each of the first prism. P1, the second prism. P2, and the third prism P3 becomes excessively small with respect to the focal length of the endoscope objective optical system. Consequently, it is not possible to make thick light rays of a light beam having a large diameter pass through the first prism P1, the second prism P2, and the third prism P3. As a result, an F-value of the endoscope objective optical system becomes large, and an image quality is degraded.

When an upper limit value of conditional expression (1) is exceeded, the size of each of the first prism P1, the second prism P2, and the third prism P3 becomes large in a radial direction of endoscope or in other words, in a direction perpendicular to a longitudinal direction of endoscope. Accordingly, an outer diameter of the optical-path deflecting prism group in the endoscope objective optical system becomes large, and the optical-path deflecting prism group cannot be built-in in the inserting portion of the endoscope.

Figure 2:
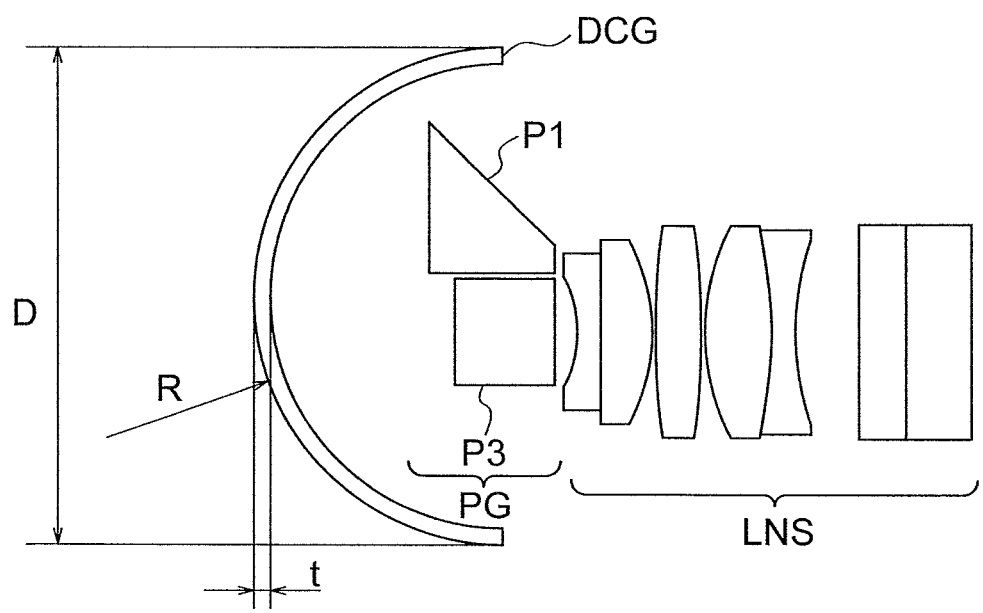
FIG. 2 is a cross-sectional view showing an arrangement of an endoscope objective optical system according to a second embodiment.
Figure 2:
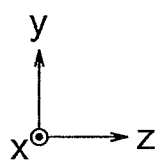

Moreover, according to a preferable aspect of the present invention, it is desirable to dispose a dome-shaped cover glass DCG between the endoscope objective optical system and an object as shown in FIG. 2, and it is desirable that a thickness t of the dome-shaped cover glass DCG satisfies the following conditional expression (2).

$$0.03 \times D \leq t \leq 0.05 \times Fno \times R \quad (2)$$

where,

D denotes an outer diameter (unit mm) of the dome-shaped cover glass DCG, t denotes the thickness (unit mm) of the dome-shaped cover glass DCG, Fno denotes an F-value of the endoscope objective optical system, and R denotes a radius of curvature (unit mm) of an object-side surface of the dome-shaped cover glass, and moreover when the outer diameter of the dome-shaped cover glass is not uniform, the largest portion is let to be the outer diameter (D), and when the thickness of the dome-shaped cover glass is not uniform, the thickest portion in an effective range is let to be the thickness (t).

Conditional expression (2) can also be expressed as follows.

$$0.03 \leq t/D \quad (2a)$$

$$t/(Fno \times R) \leq 0.05 \quad (2b)$$

Conditional expression (2) regulates an appropriate thickness t of the dome-shaped cover glass DCG. Here, since the visual-field direction is let to be variable by moving the first prism P1, the second prism P2, and the third prism P3, it is difficult to make a spherical center (center of curvature) of a dome of the hemispherical dome-shaped cover glass DCG and an entrance pupil of the endoscope objective optical system coincide. Therefore, there is a degradation of image quality due to the dome-shaped cover glass DCG. Moreover, the dome-shaped cover glass is required to have a predetermined strength as a cover glass. Therefore, it is desirable that the thickness t satisfies conditional expression (2) form a point of view of reducing degradation of image quality and securing the strength.

When an upper limit value of conditional expression (2) is exceeded, the thickness t becomes thick and the image quality is degraded. When a value falls below a lower limit value of conditional expression (2), the strength necessary as a cover glass cannot be achieved.

Figure 3A:
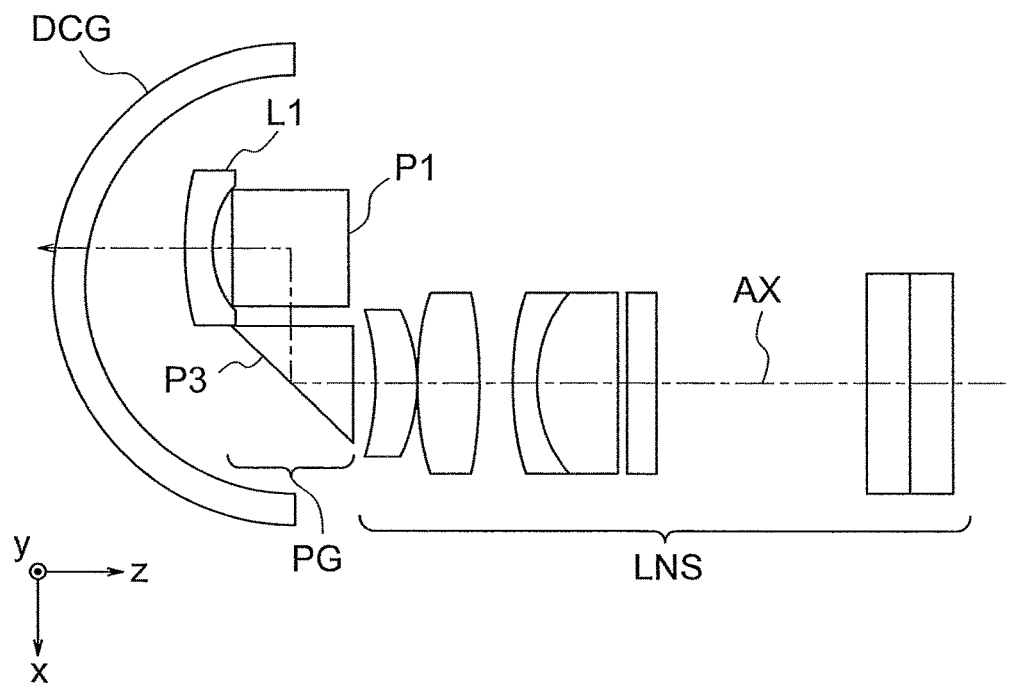
FIG. 3A is a cross-sectional view showing an arrangement of an endoscope objective optical system according to a third embodiment.
Figure 3B:
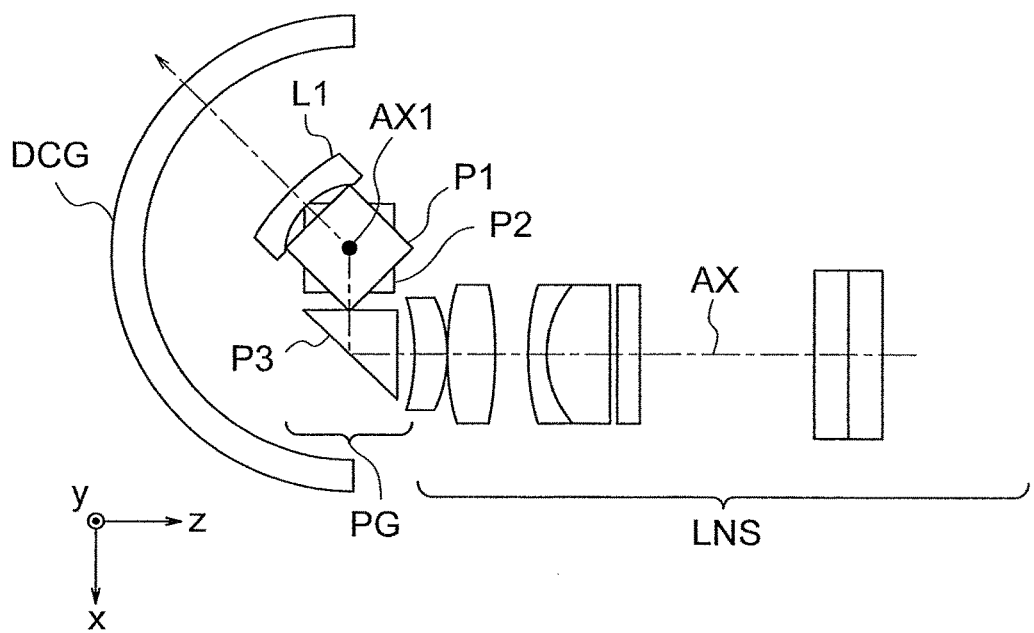
FIG. 3B is another cross-sectional view showing an arrangement of the endoscope objective optical system according to the third embodiment.
Figure 3C:
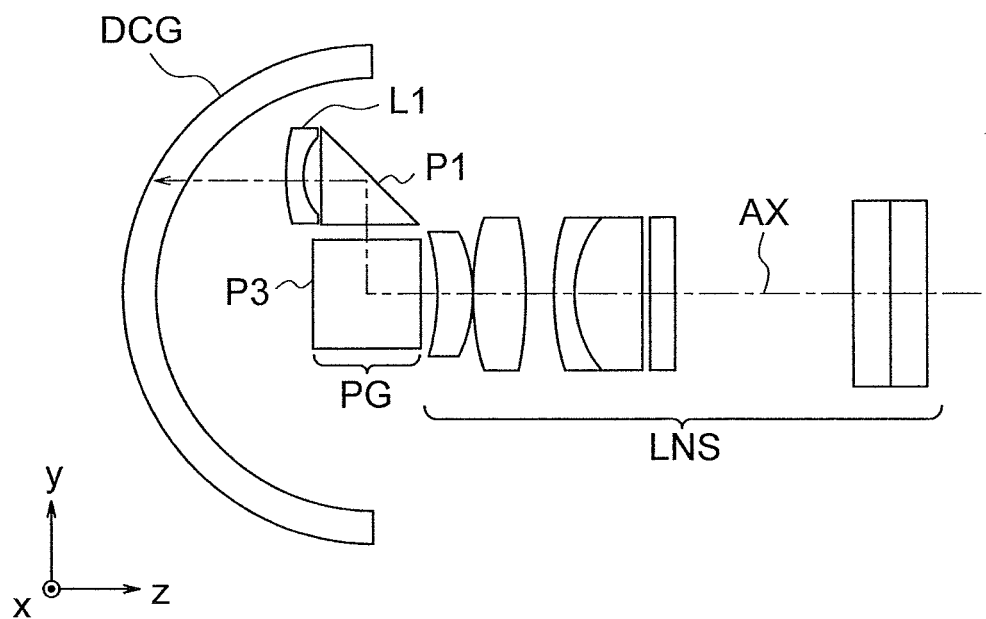
FIG. 3C is still another cross-sectional view showing an arrangement of the endoscope objective optical system according to the third embodiment.

Moreover, according to a preferable aspect of the present invention, it is desirable to dispose a dome-shaped cover glass DCG between the endoscope objective optical system and an object as shown in FIG. 3A, FIG. 3B, and FIG. 3C, and it is desirable that a center of curvature of an image-side surface of the dome-shaped cover glass DCG is positioned on an axis of rotation AX1 when the first prism P1 is made to undergo rotational movement with respect to the second prism P2, and is positioned on an axis of rotation AX2 when the first prism P1 and the second prism P2 are made to undergo rotational movement integrally with respect to the third prism P3.

FIG. 3A and FIG. 3B are diagrams illustrating an axis of rotation when the first prism P1 is made to undergo rotational movement with respect to the second prism P2. The first prism P1 undergoes rotational movement with respect to the second prism P2, with the axis of rotation AX1 as a center. The center of curvature of the image-side surface of the dome-shaped cover glass DCG is positioned on the axis of rotation AX1.

Accordingly, when a lens L1 and the first prism P1 are rotated with the axis of rotation AX1 as the center of rotation, in any of the rotating states, the lens L1 and the first prism P1 are capable of maintaining a distance from the image-side surface of the dome-shaped cover glass DCG to be constant. As a result, it is possible to prevent interference, or in other words, a contact with the dome-shaped cover glass DCG due to the rotational movement of the first prism P1. Consequently, it is possible to secure a visual-field variation range to be even wider.

Figure 3D:
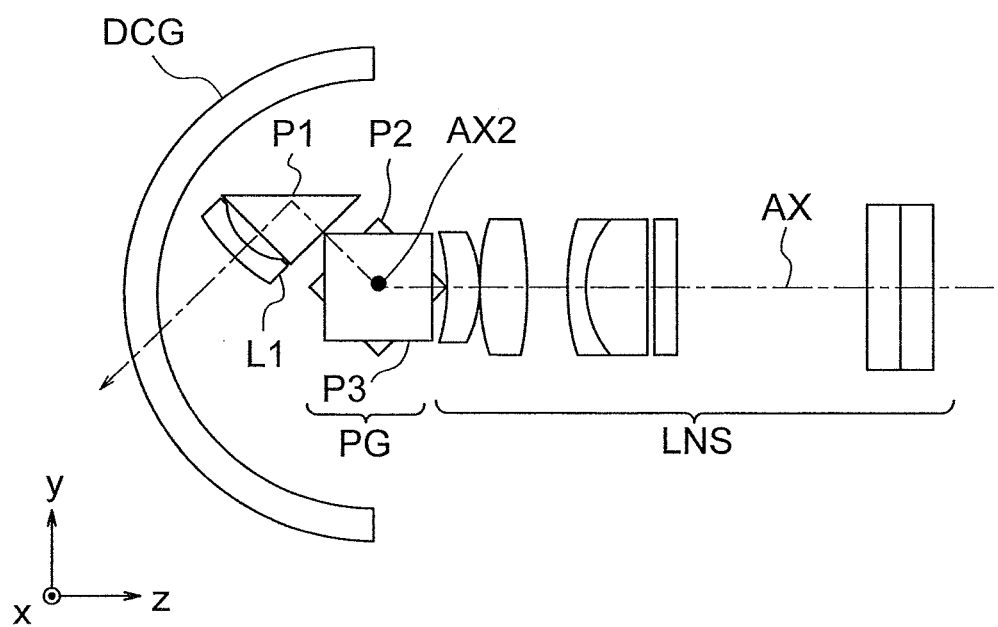
FIG. 3D is still another cross-sectional view showing an arrangement of the endoscope objective optical system according to the third embodiment.

Next, FIG. 3C and FIG. 3D are diagrams illustrating an axis of rotation when the first prism P1 and the second prism P2 are made to undergo rotational movement integrally with respect to the third prism P3. The first prism P1 and the second prism P2 undergo rotational movement integrally with the axis of rotation AX2 as a center, with respect to the third prism P3. The center of curvature of the image-side surface of the dome-shaped cover glass DCG is positioned on the axis of rotation AX2.

Accordingly, in any of the rotating states in which the lens L1 and the first prism P1, and the second prism P2 are rotated with the axis of rotation AX2 as the center of rotation, the lens L1 and the first prism P1, and the second prism P2 are capable of maintaining a constant distance from the image-side surface of the dome-shaped cover glass DCG. As a result, it is possible to prevent interference, or in other words, a contact, with the dome-shaped cover glass DCG due to the rotational movement of the lens L1 and the first prism P1, and the second prism P2. Consequently, it is possible to secure a visual-field variation range to be even wider.

Examples will be described below.

Example 1

Figure 4A:
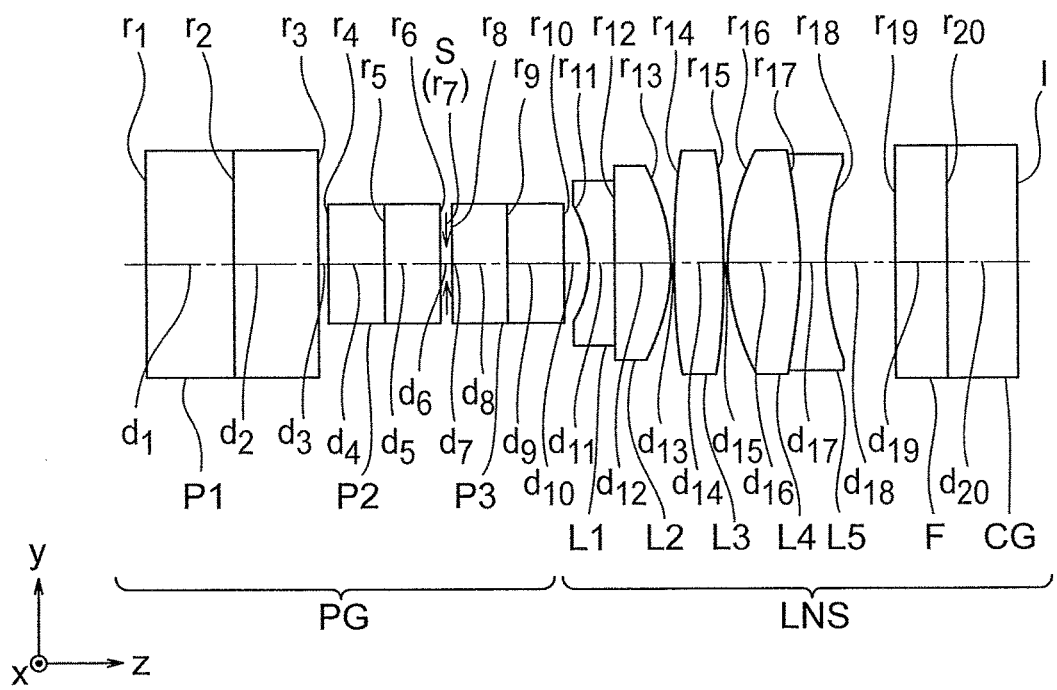
FIG. 4A is a cross-sectional view showing an arrangement of an endoscope objective optical system according to an example 1.
Figure 4B:
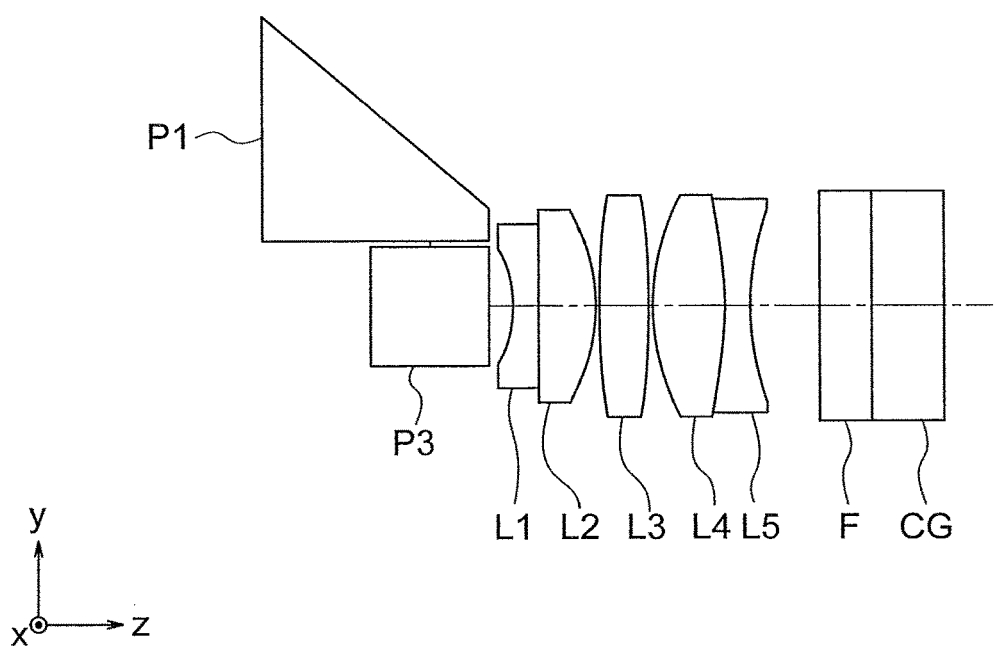
FIG. 4B is a side view of the endoscope objective optical system according to the example 1.
Figure 4C:
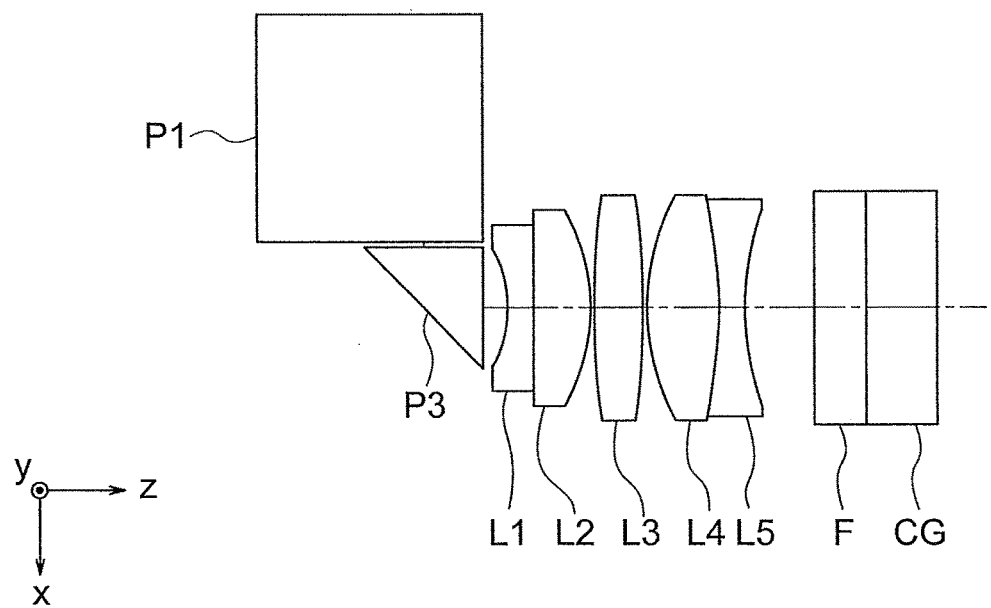
FIG. 4C is a top view of the endoscope objective optical system according to the example 1.
Figure 4D:
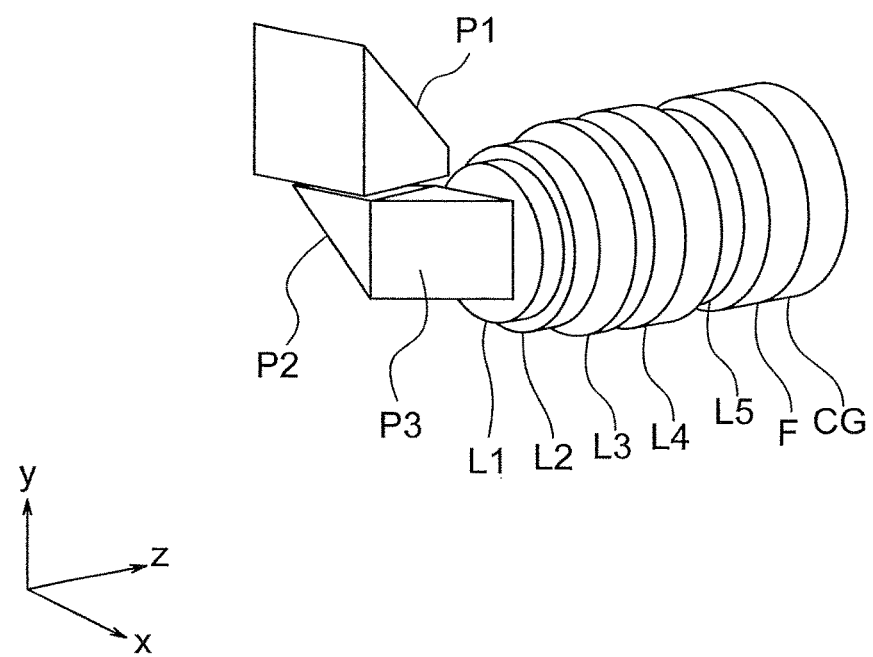
FIG. 4D is a perspective view of the endoscope objective optical system according to the example 1.

FIG. 4A, FIG. 4B, FIG. 4C, and FIG. 4D are a cross-sectional view, a side view, a top view, and a perspective view respectively, showing an arrangement of an endoscope objective optical system according to an example 1. In FIG. 4A, a prism P1, a prism P2, and a prism P3 are shown to be unfolded. Therefore, prisms are drawn as plane-parallel plates. FIG. 4B, FIG. 4C, and FIG. 4D show the first prism P1, the second prism P2, and the third prism P3 in a non-unfolded state.

The endoscope objective optical system according to the example 1 includes in order from an object side, an optical-path deflecting prism group PG and a lens group LNS. The optical-path deflecting prism group PG includes a first prism P1, a second prism P2, an aperture stop S, and a third prism P3.

The lens group LNS includes in order from the object side, a concavoplane negative lens L1 having a concave surface directed toward the object side, a planoconvex positive lens L2 having a convex surface directed toward an image side, a biconvex positive lens L3, a biconvex positive lens L4, a biconcave negative lens L5, a plane-parallel plate F, and a plane-parallel plate CG. Here, the concavoplane negative lens L1 and the planoconvex positive lens L2 are cemented. Moreover, the biconvex positive lens L4 and the biconcave negative lens L5 are cemented.

The plane-parallel plate F is an infrared absorbing filter with a YAG (Yttrium Aluminum Garnet) laser cut coating applied to an object side thereof and an LD laser cut coating applied to an image side thereof.

Example 2

Figure 5A:
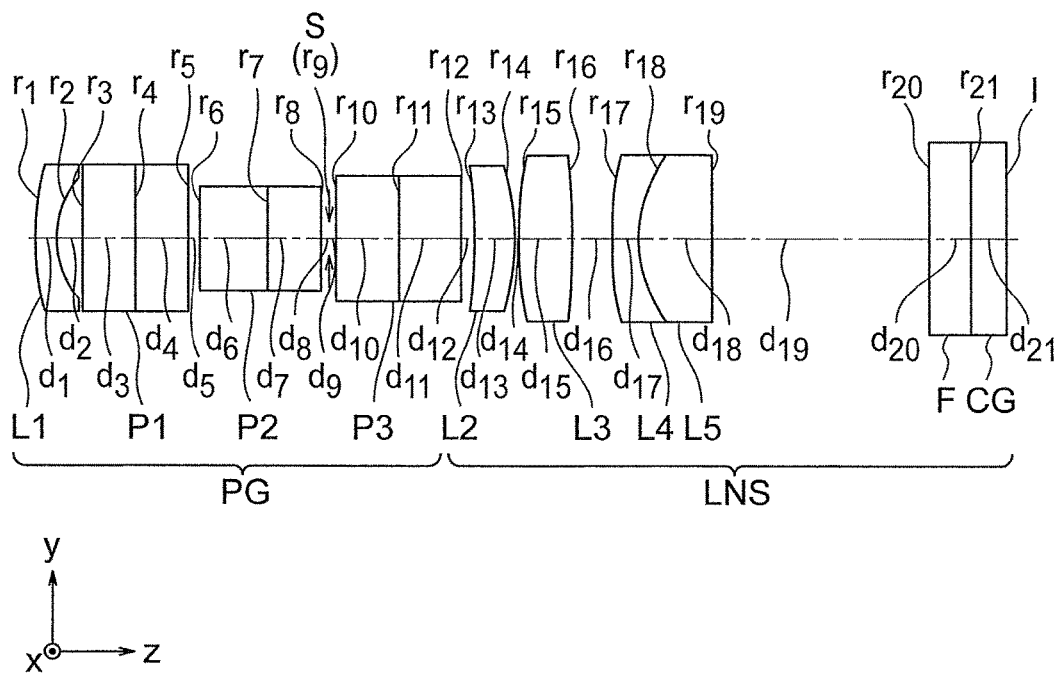
FIG. 5A is a cross-sectional view showing an arrangement of an endoscope objective optical system according to an example 2.
Figure 5B:
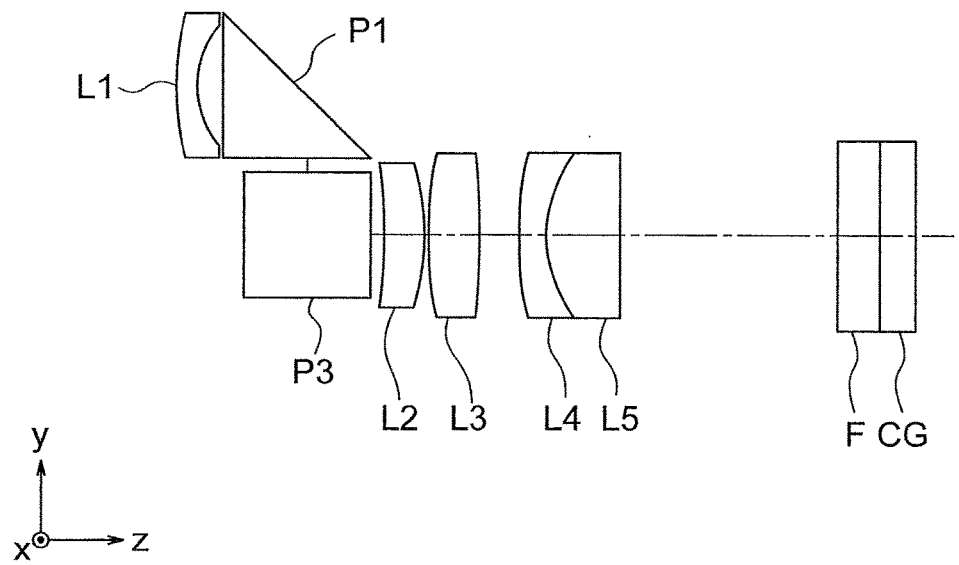
FIG. 5B is a side view of the endoscope objective optical system according to the example 2.
Figure 5C:
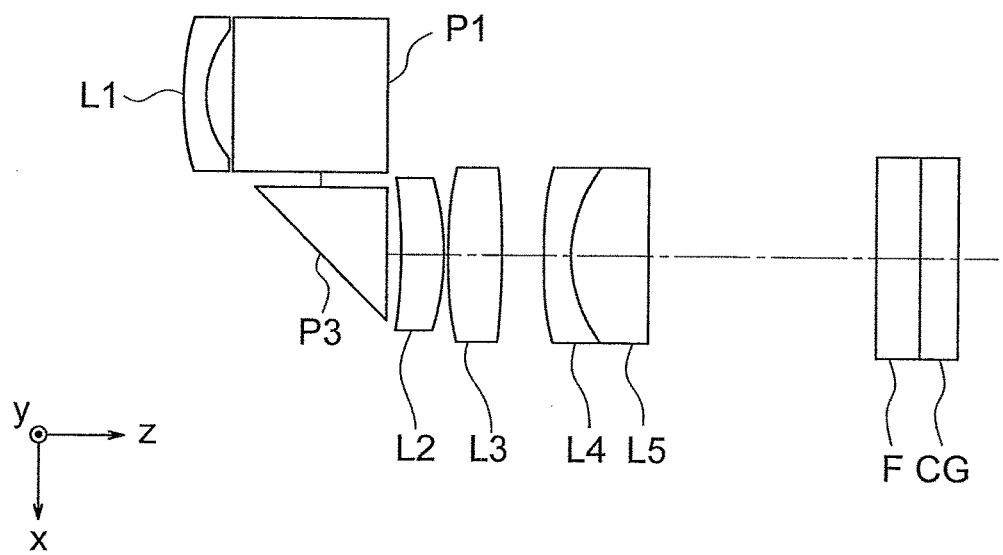
FIG. 5C is a top view of the endoscope objective optical system according to the example 2.
Figure 5D:
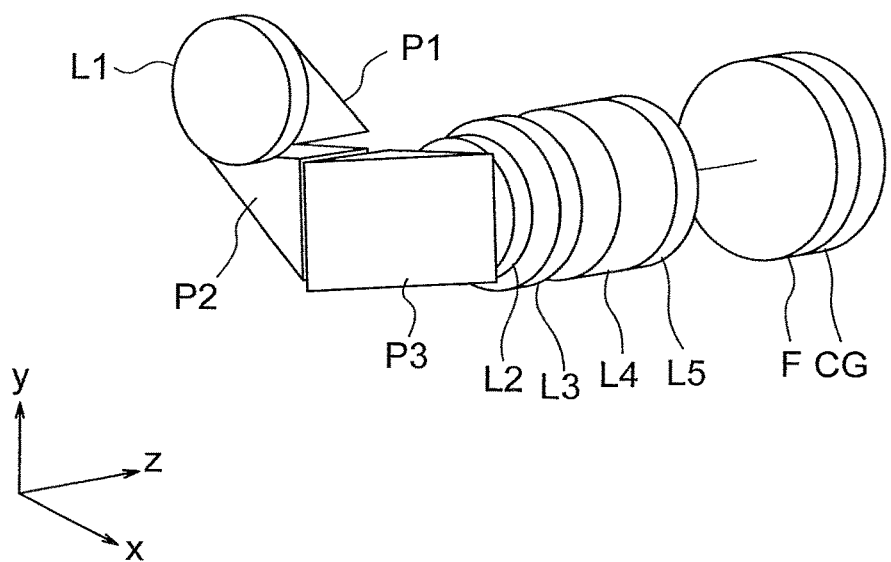
FIG. 5D is a perspective view of the endoscope objective optical system according to the example 2.

FIG. 5A, FIG. 5B, FIG. 5C, and FIG. 5D are a cross-sectional view, a side view, a top view, and a perspective view respectively, showing an arrangement of an endoscope objective optical system according to an example 2. In FIG. 5A, a first prism P1, a second prism P2, and a third prism P3 are shown to be unfolded. Therefore, the prisms are drawn as plane-parallel plates. FIG. 5B, FIG. 5C, and FIG. 5D show the first prism P1, the second prism P2, and the third prism P3 in a non-unfolded state.

The endoscope objective optical system according to the example 2 includes in order from an object side, an optical-path deflecting prism group PG and a lens group LNS. The optical-path deflecting prism group PG includes a negative meniscus lens L1 having a convex surface directed toward the object side, the first prism P1, the second prism P2, an aperture stop S, and the third prism P3.

The lens group LNS includes in order from the object side, a positive meniscus lens L2 having a convex surface directed toward an image side, a biconvex positive lens L3, a negative meniscus lens L4 having a convex surface directed toward the object side, a convexoplane positive lens L5 having a convex surface directed toward the object side, a plane-parallel plate F, and a plane-parallel plate CG. Here, the negative meniscus lens L4 and the convexoplane positive lens L5 are cemented.

Example 3

Figure 6A:
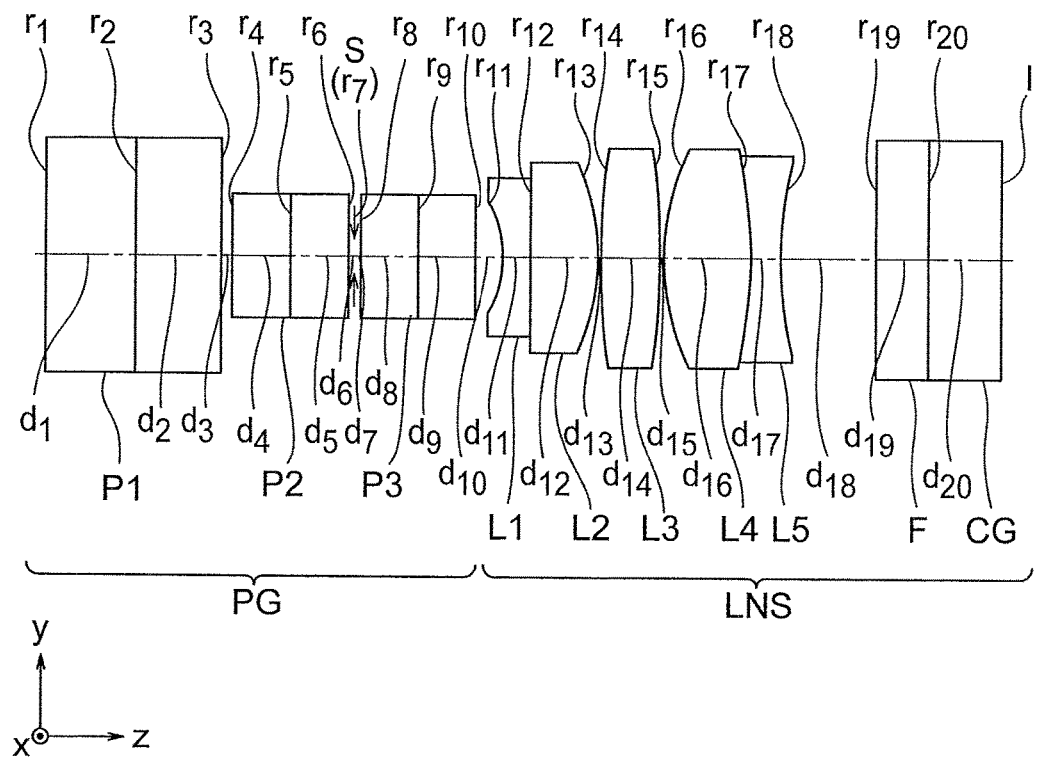
FIG. 6A is a cross-sectional view showing an arrangement of an endoscope objective optical system according to an example 3.
Figure 6B:
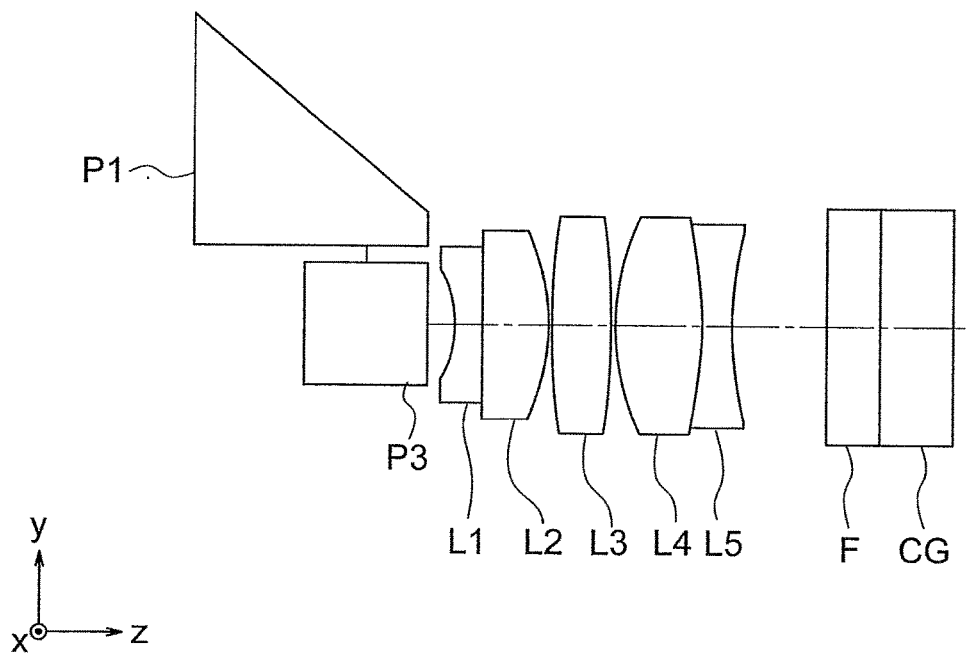
FIG. 6B is a side view of the endoscope objective optical system according to the example 3.
Figure 6C:
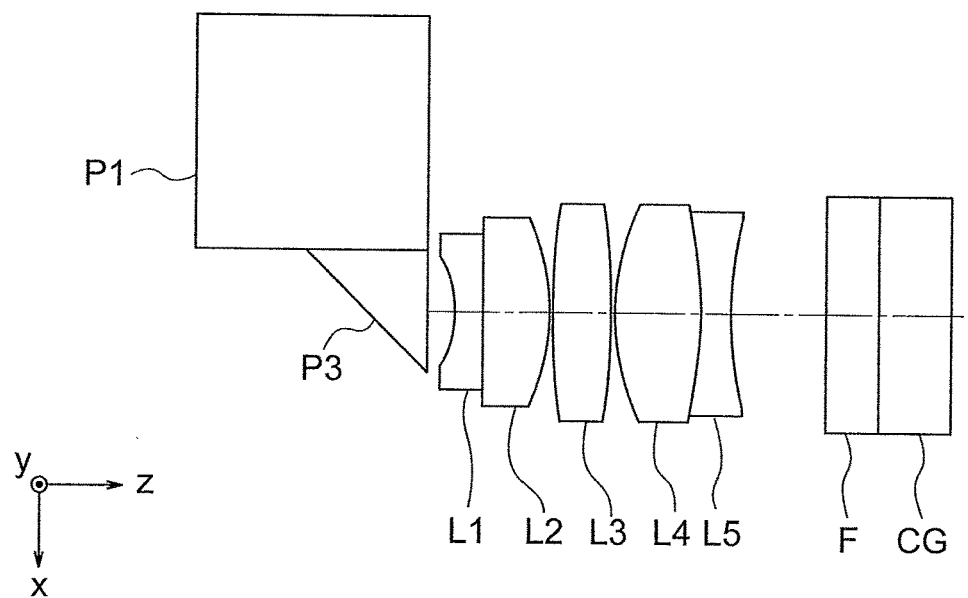
FIG. 6C is a top view of the endoscope objective optical system according to the example 3.
Figure 6D:
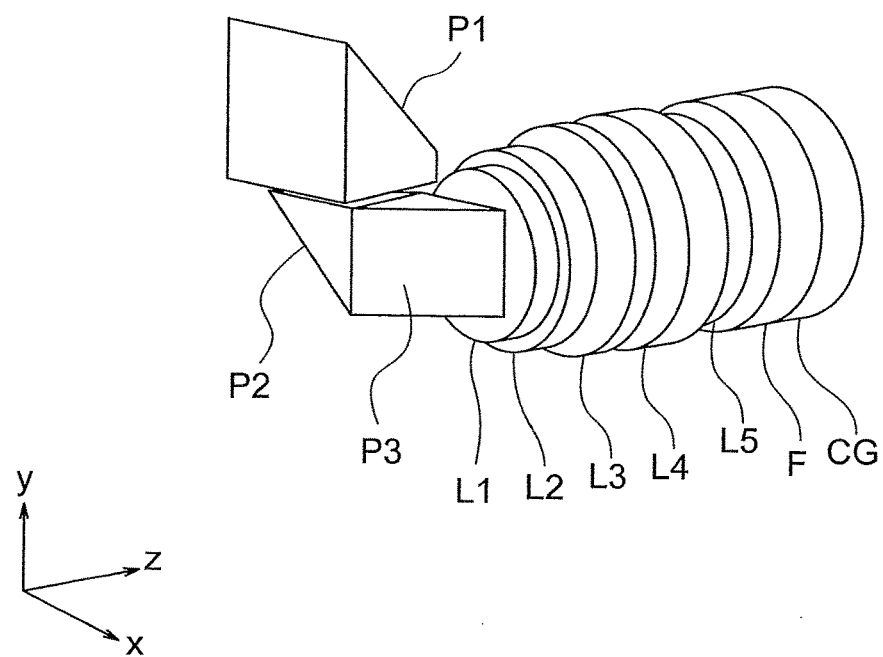
FIG. 6D is a perspective view of the endoscope objective optical system according to the example 3.

FIG. 6A, FIG. 6B, FIG. 6C, and FIG. 6D are a cross-sectional view, a side view, a top view, and a perspective view respectively, of an endoscope objective optical system according to an example 3. In FIG. 6A, a first prism P1, a second prism P2, and a third prism P3 are shown to be unfolded. Therefore, the prisms are drawn as plane-parallel plates. FIG. 6B, FIG. 6C, and FIG. 6D show the first prism P1, the second prism P2, and the third prism P3 in a non-unfolded state.

The endoscope objective optical system according to the example 3 includes in order from an object side, an optical-path deflecting prism group PG and a lens group LNS. The optical-path deflecting prism group PG includes the first prism P1, the second prism P2, an aperture stop S, and the third prism P3.

The lens group LNS includes in order from the object side, a concavoplane negative lens L1 having a concave surface directed toward the object side, a planoconvex positive lens L2 having a convex surface directed toward an image side, a biconvex positive lens L3, a biconvex positive lens L4, a biconcave negative lens L5, a plane-parallel plate F, and a plane-parallel plate CG. Here, the concavoplane negative lens L1 and the planoconvex positive lens L2 are cemented. Moreover, the biconvex positive lens L4 and the biconcave negative lens L5 are cemented.

The plane-parallel plate F is an infrared absorbing filter with a YAG laser cut coating applied to an object side thereof and an LD laser cut coating applied to an image side thereof.

Example 4

Figure 7A:
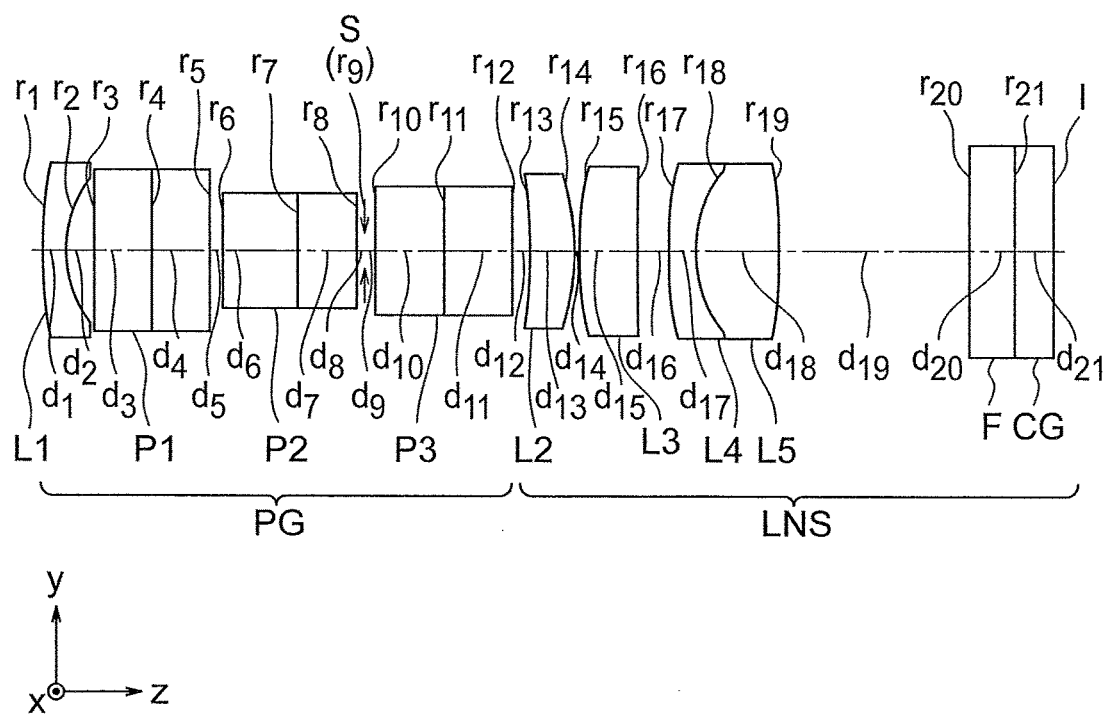
FIG. 7A is a cross-sectional view showing an arrangement of an endoscope objective optical system according to an example 4.
Figure 7B:
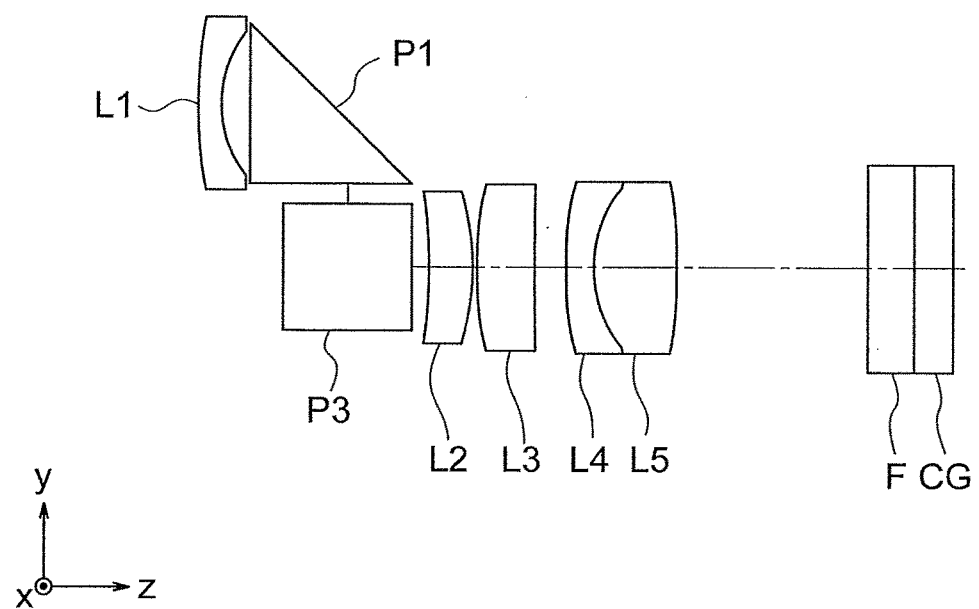
FIG. 7B is a side view of the endoscope objective optical system according to the example 4.
Figure 7C:
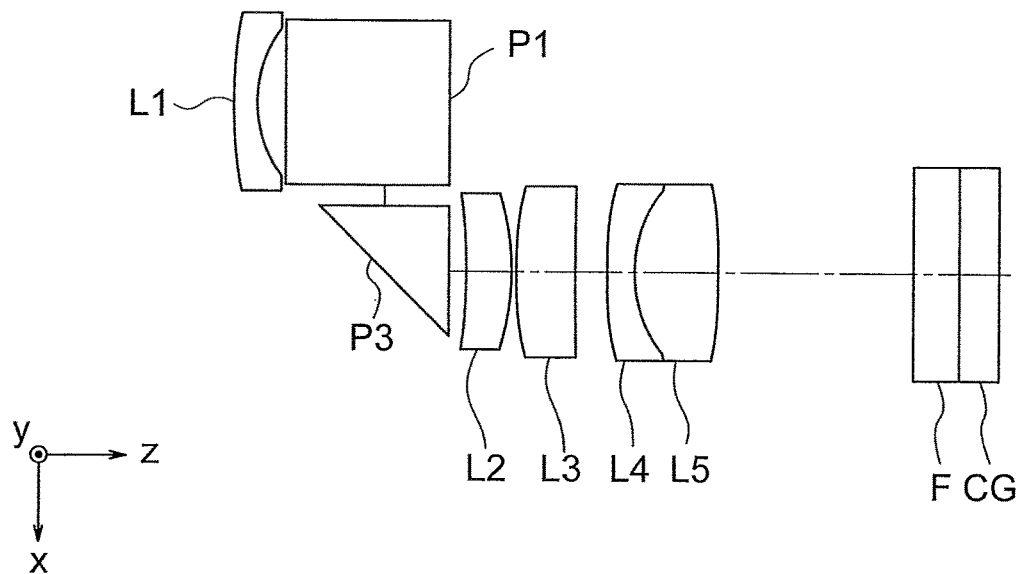
FIG. 7C is a top view of the endoscope objective optical system according to the example 4.
Figure 7D:
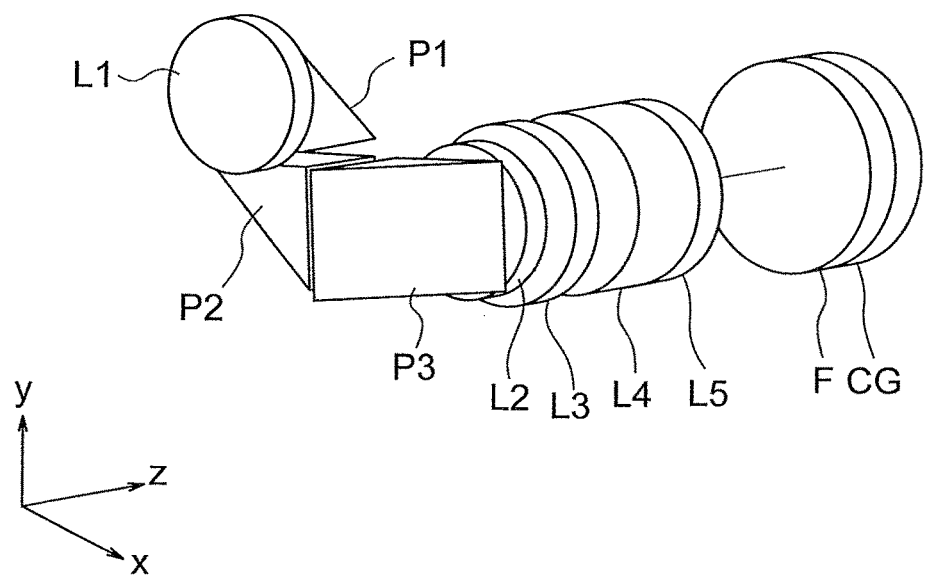
FIG. 7D is a perspective view of the endoscope objective optical system according to the example 4.

FIG. 7A, FIG. 7B, FIG. 7C, and FIG. 7D are a cross-sectional view, a side view, a top view, a perspective view respectively, of an endoscope objective optical system according to an example 4. In FIG. 7A, a first prism P1, a second prism P2, and a third prism P3 are shown to be unfolded. Therefore, the prisms are drawn as plane-parallel plates. FIG. 7B, FIG. 7C, and FIG. 7D show the first prism P1, the second prism P2, and the third prism P3 in a non-unfolded state.

The endoscope objective optical system according to the example 4 includes in order from an object side, an optical-path deflecting prism group PG and a lens group LNS. The optical-path deflecting prism group PG includes a negative meniscus lens L1 having a convex surface directed toward the object side, the first prism P1, the second prism P2, an aperture stop S, and the third prism P3.

The lens group LNS includes in order from the object side, a positive meniscus lens L2 having a convex surface directed toward an image side, a positive meniscus lens L3 having a convex surface directed toward the object side, a negative meniscus lens L4 having a convex surface directed toward the object side, a biconvex positive lens L5, a plane-parallel plate F, and a plane-parallel plate CG. Here, the negative meniscus lens L4 and the biconvex positive lens L5 are cemented.

The plane-parallel plate F is an infrared absorbing filter with a YAG laser cut coating applied to an object side thereof and an LD laser cut coating applied to an image side thereof.

Example 5

Figure 8A:
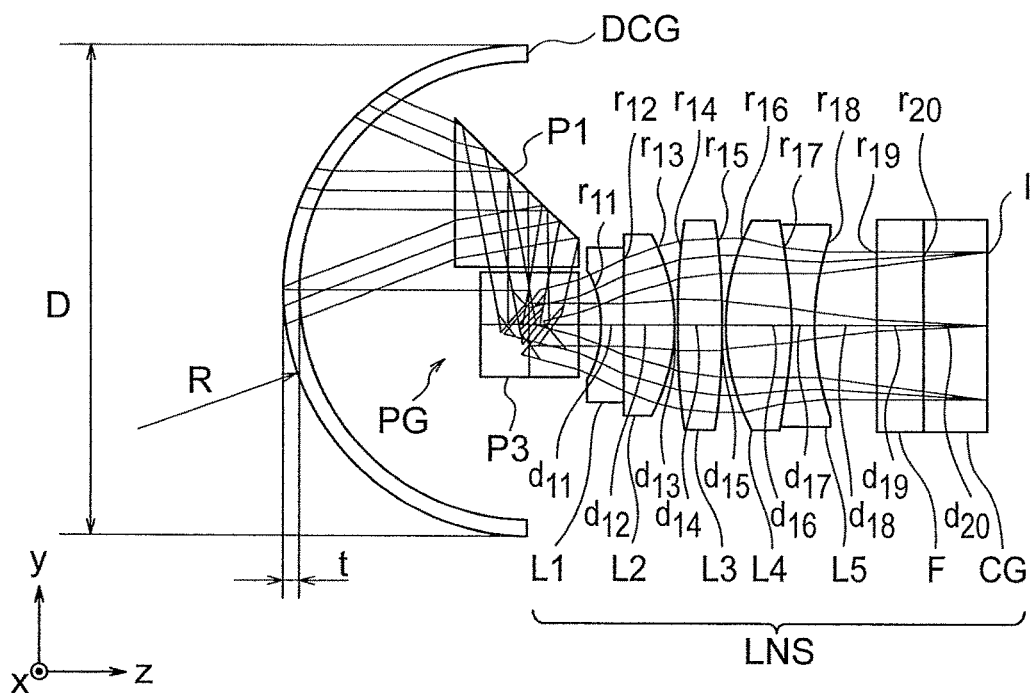
FIG. 8A is a side view of an endoscope objective optical system according to an example 5.
Figure 8B:
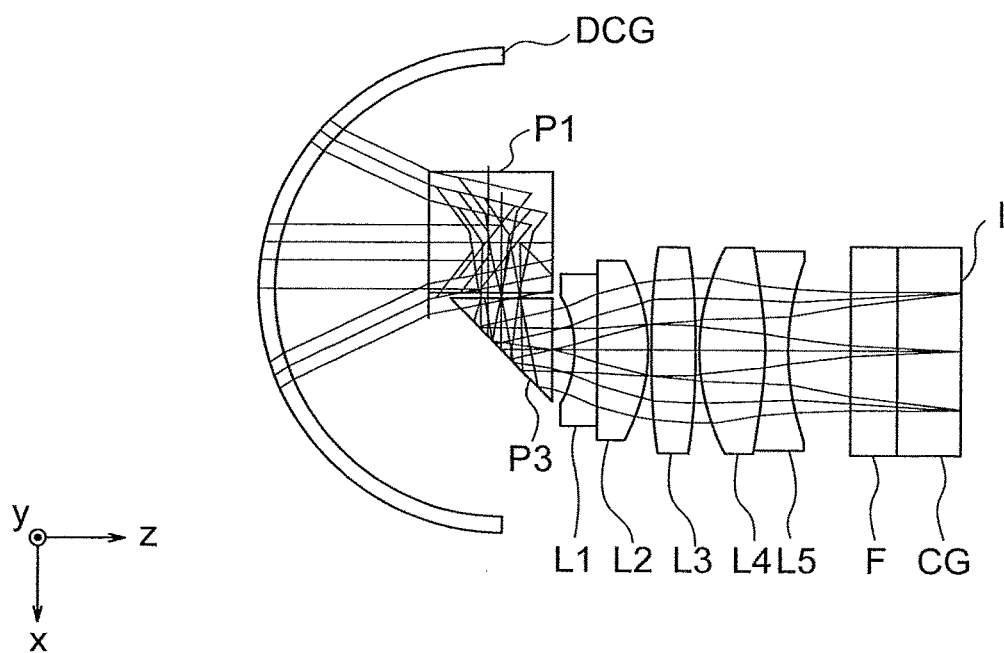
FIG. 8B is a top view of the endoscope objective optical system according to the example 5.

FIG. 8A and FIG. 8B are a side view and a top view respectively, of an endoscope objective optical system according to an example 5. In FIG. 8A and FIG. 8B, a first prism P1, a second prism P2, and a third prism P3 are shown to be in a non-unfolded state.

The endoscope objective optical system according to the example 5 includes in order from an object side, a dome-shaped cover glass DCG, an optical-path deflecting prism group PG, and a lens group LNS. The optical-path deflecting prism group PG includes the first prism 21, the second prism P2, an aperture stop S, and the third prism P3.

The lens group LNS includes in order from the object side, a concavoplane negative lens L1 having a concave surface directed toward the object side, a planoconvex positive lens L2 having a convex surface directed toward an image side, a biconvex positive lens L3, a biconvex positive lens L4, a biconcave negative lens L5, a plane-parallel plate F, and a plane-parallel plate CG. Here, the concavoplane negative lens L1 and the planoconvex positive lens L2 are cemented. Moreover, the biconvex positive lens L4 and the biconcave negative lens L5 are cemented.

The plane-parallel plate F is an infrared absorbing filter with a YAG laser cut coating applied to an object side thereof and an LD laser cut coating applied to an image side thereof.

Example 6

Figure 9A:
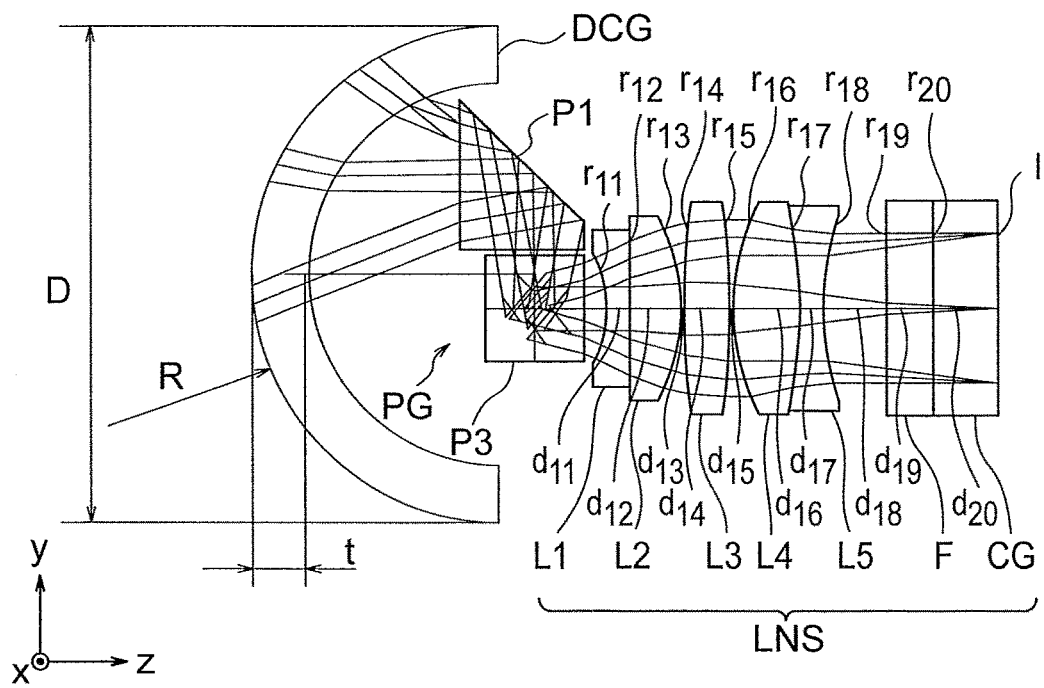
FIG. 9A is a side view of an endoscope objective optical system according to an example 6.
Figure 9B:
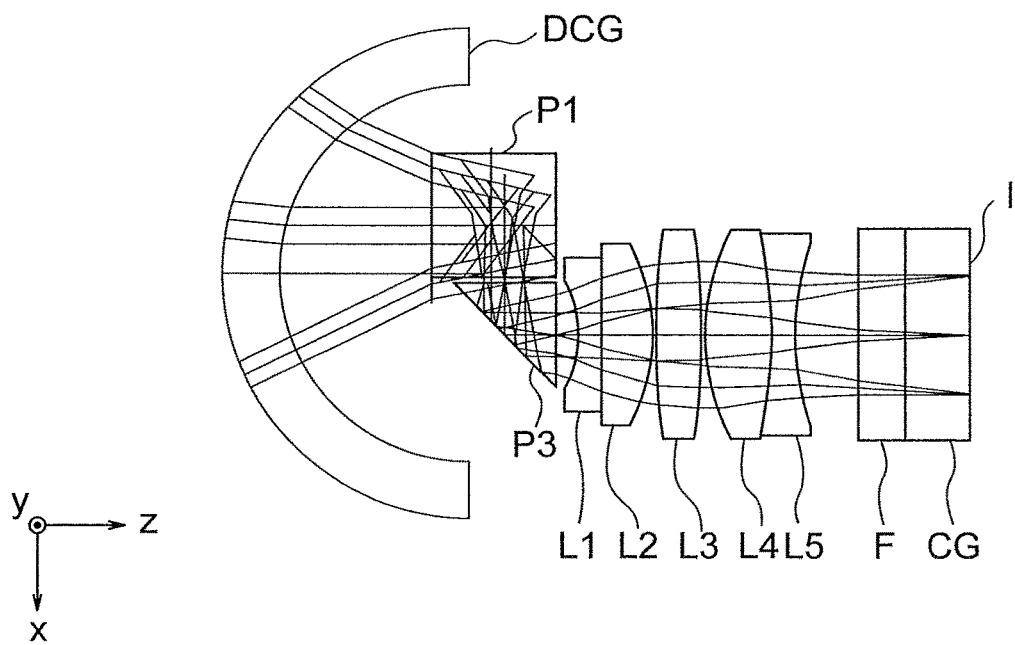
FIG. 9B is a top view of the endoscope objective optical system according to the example 6.

FIG. 9A and FIG. 9B are a side view and a top view respectively, of an endoscope objective optical system according to an example 6. In FIG. 9A and FIG. 9B, a first prism P1, a second prism P2, and a third prism P3 are shown to be in a non-unfolded state.

The endoscope objective optical system according to the example 6 includes in order from an object side, a dome-shaped cover glass DCG, an optical-path deflecting prism group PG, and a lens group LNS. The optical-path deflecting prism group PG includes the first prism P1, the second prism P2, an aperture stop S, and the third prism P3.

The lens group LNS includes in order from the object side, a concavoplane negative lens L1 having a concave surface directed toward the object side, a planoconvex positive lens L2 having a convex surface directed toward an image side, a biconvex positive lens L3, a biconvex positive lens L4, a biconcave negative lens L5, a plane-parallel plate F, and a plane-parallel plate CG. Here, the concavoplane negative lens L1 and the planoconvex positive lens L2 are cemented. Moreover, the biconvex positive lens L4 and the biconcave negative lens L5 are cemented.

The plane-parallel plate F is an infrared absorbing filter with a YAG laser cut coating applied to an object side thereof and an LD laser cut coating applied to an image side thereof.

Example 7

Figure 10A:
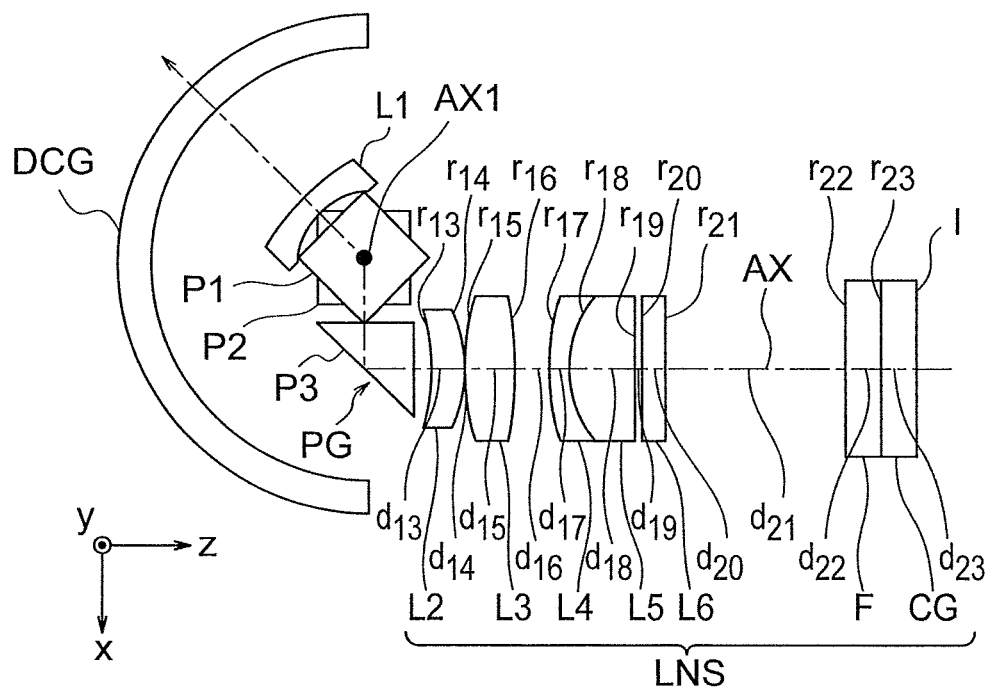
FIG. 10A is a top view of an endoscope objective optical system according to an example 7.
Figure 10B:
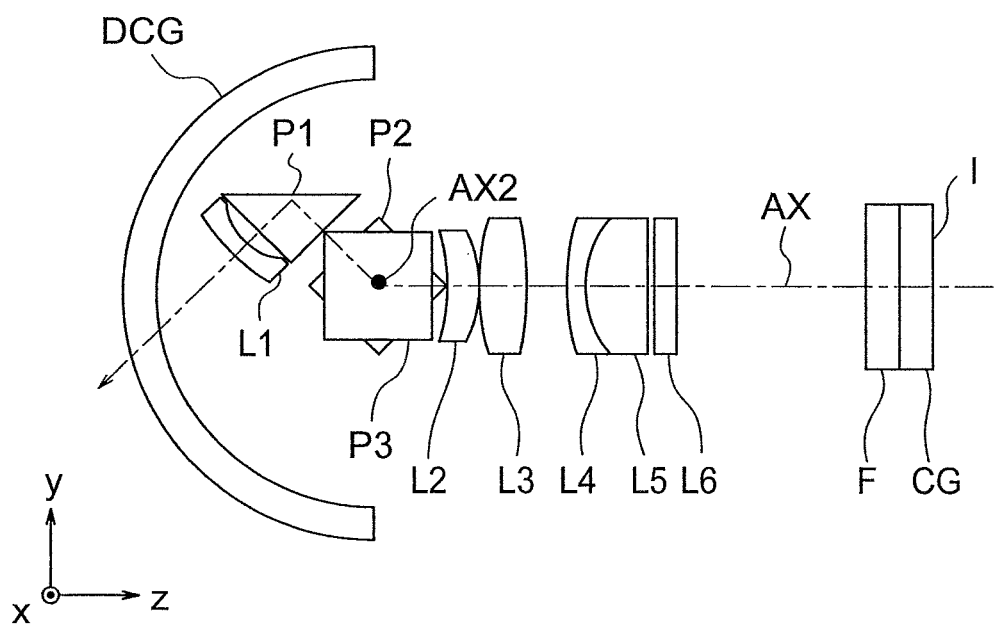
FIG. 10B is a side view of the endoscope objective optical system according to the example 7.

FIG. 10A and FIG. 10B are a top view and a side view respectively, of an endoscope objective optical system according to an example 7. In FIG. 10A and FIG. 10B, a first prism P1, a second prism P2, and a third prism P3 are shown to be in a non-unfolded state.

The endoscope objective optical system according to the example 7 includes in order from an object side, a dome-shaped cover glass DCG, an optical-path deflecting prism group PG, and a lens group LNS. The optical-path deflecting prism group PG includes a negative meniscus lens L1 having a convex surface directed toward the object side, the first prism. P1, the second prism P2, an aperture stop S, and the third prism P3.

The lens group LNS includes in order from the object side, a positive meniscus lens L2 having a convex surface directed toward an image side, a biconvex positive lens L3, a negative meniscus lens L4 having a convex surface directed toward the object side, a convexoplane positive lens L5 having a convex surface directed toward the object side, a plane-parallel plate L6, a plane-parallel plate F, and a plane-parallel plate CG. Here, the negative meniscus lens L4 and the convexoplane positive lens L5 are cemented.

The plane-parallel plate F is an infrared absorbing filter with a YAG laser cut coating applied to an object side thereof and an LD laser cut coating applied to an image side thereof.

Numerical data for each example is shown below. Regarding symbols, apart from the symbols mentioned above, r denotes a radius of curvature of each lens surface, d denotes a distance between two lens surfaces, nd denotes a refractive index of each lens for a d-line, and νd denotes Abbe's number for each lens. Moreover, FL denotes a focal length of the overall system, Fno denotes an F-value, ω denotes a half angle of view, and L denotes a total air conversion length (unit mm) of the first prism, the second prism, and the third prism in the optical-path deflecting prism group. Here, the total air conversion length is a value obtained by summing up a value obtained by dividing a length of an optical axis passing through the first prism by a refractive index for the d-line nd1 of a glass material of the first prism, a value obtained by dividing a length of an optical axis passing through the second prism by a refractive index for the d-line nd2 of a glass material of the second prism, and a value obtained by dividing a length of an optical axis passing through the third prism by a refractive index for the d-line nd3 of a glass material of the third prism. Moreover, a reflecting surface is marked with '*'.

Example 1

Unit mm

Surface data

| Surface no. | r | d | nd | νd |
|---|---|---|---|---|
| Object plane | ∞ | 35.230 | | |
| 1 | ∞ | 0.415 | 1.883 | 40.765 |
| 2* | ∞ | 0.415 | 1.883 | 40.765 |
| 3 | ∞ | 0.050 | | |
| 4 | ∞ | 0.277 | 1.883 | 40.765 |
| 5* | ∞ | 0.277 | 1.883 | 40.765 |
| 6 | ∞ | 0.025 | | |
| 7(Stop) | ∞ | 0.025 | | |
| 8 | ∞ | 0.277 | 1.883 | 40.765 |
| 9* | ∞ | 0.277 | 1.883 | 40.765 |
| 10 | ∞ | 0.116 | | |
| 11 | −0.652 | 0.126 | 1.518 | 58.902 |
| 12 | ∞ | 0.277 | 1.883 | 40.765 |
| 13 | −0.983 | 0.015 | | |
| 14 | 3.984 | 0.252 | 1.883 | 40.765 |
| 15 | −3.162 | 0.015 | | |
| 16 | 1.166 | 0.352 | 1.693 | 50.811 |
| 17 | −2.585 | 0.126 | 1.959 | 17.471 |
| 18 | 1.622 | 0.338 | | |
| 19 | ∞ | 0.252 | 1.516 | 64.142 |
| 20 | ∞ | 0.352 | 1.614 | 50.200 |
| Image pickup surface | ∞ | | | |

Various data

| | |
|---|---|
| FL | 1 |
| L | 1.029 |
| Fno | 4.55 |
| ω | 60° |

Example 2

Unit mm

Surface data

| Surface no. | r | d | nd | νd |
|---|---|---|---|---|
| Object plane | ∞ | 25.253 | | |
| 1 | 1.852 | 0.126 | 1.806098 | 40.926 |
| 2 | 0.616 | 0.149 | | |
| 3 | ∞ | 0.316 | 2.003300 | 28.273 |
| 4* | ∞ | 0.316 | 2.003300 | 28.273 |
| 5 | ∞ | 0.063 | | |
| 6 | ∞ | 0.410 | 2.003300 | 28.273 |
| 7* | ∞ | 0.316 | 2.003300 | 28.273 |
| 8 | ∞ | 0.076 | | |
| 9(Stop) | ∞ | 0.019 | | |
| 10 | ∞ | 0.379 | 2.003300 | 28.273 |
| 11* | ∞ | 0.379 | 2.003300 | 28.273 |
| 12 | ∞ | 0.082 | | |
| 13 | −2.751 | 0.253 | 1.806098 | 40.882 |
| 14 | −1.547 | 0.019 | | |
| 15 | 2.321 | 0.316 | 1.882997 | 40.765 |
| 16 | −5.742 | 0.237 | | |
| 17 | 2.179 | 0.158 | 1.846660 | 23.778 |
| 18 | 0.804 | 0.442 | 1.496999 | 81.546 |
| 19 | ∞ | 1.313 | | |
| 20 | ∞ | 0.253 | 1.516330 | 64.142 |
| 21 | ∞ | 0.221 | 1.613500 | 50.200 |
| Image pickup surface | ∞ | | | |

Various data

| | |
|---|---|
| FL | 1 |
| L | 1.056 |
| Fno | 4.48 |
| ω | 60° |

Example 3

Unit mm

Surface data

| Surface no. | r | d | nd | νd |
|---|---|---|---|---|
| Object plane | ∞ | 30.822 | | |
| 1 | ∞ | 0.363 | 1.883 | 40.765 |
| 2* | ∞ | 0.363 | 1.883 | 40.765 |
| 3 | ∞ | 0.044 | | |

-continued

Unit mm

| | | | | |
|---|---|---|---|---|
| 4 | ∞ | 0.242 | 1.883 | 40.765 |
| 5* | ∞ | 0.242 | 1.883 | 40.765 |
| 6 | ∞ | 0.022 | | |
| 7(Stop) | ∞ | 0.022 | | |
| 8 | ∞ | 0.242 | 1.883 | 40.765 |
| 9* | ∞ | 0.242 | 1.883 | 40.765 |
| 10 | ∞ | 0.101 | | |
| 11 | −0.652 | 0.126 | 1.518 | 58.90 |
| 12 | ∞ | 0.277 | 1.883 | 40.765 |
| 13 | −0.983 | 0.015 | | |
| 14 | 3.984 | 0.252 | 1.883 | 40.765 |
| 15 | −3.162 | 0.015 | | |
| 16 | 1.166 | 0.352 | 1.693 | 50.811 |
| 17 | −2.585 | 0.126 | 1.959 | 17.471 |
| 18 | 1.622 | 0.390 | | |
| 19 | ∞ | 0.220 | 1.516 | 64.142 |
| 20 | ∞ | 0.308 | 1.614 | 50.200 |
| Image pickup surface | ∞ | | | |

Various data

| | |
|---|---|
| FL | 1 |
| L | 0.9 |
| Fno | 5.2 |
| ω | 50° |

Example 4

Unit mm

Surface data

| Surface no. | r | d | nd | vd |
|---|---|---|---|---|
| Object plane | ∞ | 35.852 | | |
| 1 | 5.617835 | 0.1791428 | 1.806098 | 40.925996 |
| 2 | 0.819238 | 0.2025591 | | |
| 3 | ∞ | 0.4477511 | 2.003300 | 28.27328 |
| 4* | ∞ | 0.4477511 | 2.003300 | 28.27328 |
| 5 | ∞ | 0.08955022 | | |
| 6 | ∞ | 0.5820765 | 2.003300 | 28.27328 |
| 7* | ∞ | 0.4477511 | 2.003300 | 28.27328 |
| 8 | ∞ | 0.1074603 | | |
| 9(Stop) | ∞ | 0.02686507 | | |
| 10 | ∞ | 0.5373013 | 2.003300 | 28.27328 |
| 11* | ∞ | 0.5373013 | 2.003300 | 28.27328 |
| 12 | ∞ | 0.1164153 | | |
| 13 | −13.4875 | 0.3582857 | 1.806098 | 40.881692 |
| 14 | −2.391508 | 0.02686507 | | |
| 15 | 2.447604 | 0.4477511 | 1.882997 | 40.765107 |
| 16 | 18.23645 | 0.2325315 | | |
| 17 | 2.986169 | 0.2238756 | 1.846660 | 23.77794 |
| 18 | 1.052876 | 0.6268516 | 1.496999 | 81.545888 |
| 19 | −5.667179 | 1.478543 | | |
| 20 | ∞ | 0.3582857 | 1.516330 | 64.142022 |
| 21 | ∞ | 0.3134258 | 1.613500 | 50.2 |
| Image pickup surface | ∞ | | | |

Various data

| | |
|---|---|
| FL | 1 |
| L | 1.498 |
| Fno | 3.73 |
| ω | 88.6° |

Examples 5, 6

Unit mm

Surface data

| Surface no. | r | d | nd | vd |
|---|---|---|---|---|
| Object plane | ∞ | 70 | | |
| 1 | ∞ | 0.825 | 1.882997 | 40.765 |
| 2* | ∞ | 0.825 | 1.882997 | 40.765 |
| 3 | ∞ | 0.1 | | |
| 4 | ∞ | 0.55 | 1.882997 | 40.76 |
| 5* | ∞ | 0.55 | 1.882997 | 40.765 |
| 6 | ∞ | 0.1 | | |
| 7(Stop) | ∞ | 0 | | |
| 8 | ∞ | 0.55 | 1.882997 | 40.765 |
| 9* | ∞ | 0.55 | 1.882997 | 40.765 |
| 10 | ∞ | 0.23 | | |
| 11 | −1.295 | 0.25 | 1.518229 | 58.902 |
| 12 | ∞ | 0.55 | 1.882997 | 40.765 |
| 13 | −1.953 | 0.03 | | |
| 14 | 7.916 | 0.5 | 1.882997 | 40.765 |
| 15 | −6.283 | 0.03 | | |
| 16 | 2.316 | 0.7 | 1.693495 | 50.811 |
| 17 | −5.137 | 0.25 | 1.959060 | 17.471 |
| 18 | 3.222 | 0.658 | | |
| 19 | ∞ | 0.5 | 1.516330 | 64.142 |
| 20 | ∞ | 0.7 | 1.617722 | 49.832 |
| Image pickup surface | ∞ | | | |

Various data

| | |
|---|---|
| FL | 1.99 |
| L | 2.045 |
| Fno | 4.55 |
| ω | 60° | dome-shaped cover glass

| | |
|---|---|
| glass material | sapphire |
| outer diameter D | 5.4 |
| radius of curvature of an object-side surface R | 2.7 |
| thickness t | 0.17 |

Example 6

| | |
|---|---|
| FL | 1.99 |
| L | 2.045 |
| Fno | 4.55 |
| ω | 60° | dome-shaped cover glass

| | |
|---|---|
| glass material | sapphire |
| outer diameter D | 5.4 |
| radius of curvature of an object-side surface R | 2.7 |
| thickness t | 0.6 |

Example 7

Unit mm

Surface data

| Surface no. | r | d | nd | vd |
|---|---|---|---|---|
| Object plane | ∞ | 40.00947 | | |
| 1 | 2.932838 | 0.2000473 | 1.806098 | 40.925996 |

-continued

| Unit mm | | | | |
|---|---|---|---|---|
| 2 | 0.9752386 | 0.2364146 | | |
| 3 | ∞ | 0.5 | 2.003300 | 28.273280 |
| 4* | ∞ | 0.5 | 2.003300 | 28.273280 |
| 5 | ∞ | 0.1 | | |
| 6 | ∞ | 0.65 | 2.003300 | 28.273280 |
| 7* | ∞ | 0.5 | 2.003300 | 28.273280 |
| 8 | ∞ | 0.12 | | |
| 9(Stop) | ∞ | 0.03 | | |
| 10 | ∞ | 0.600142 | 2.003300 | 28.273280 |
| 11* | ∞ | 0.600142 | 2.003300 | 28.273280 |
| 12 | ∞ | 0.13 | | |
| 13 | −4.357899 | 0.4000947 | 1.806098 | 40.881692 |
| 14 | −2.450486 | 0.03 | | |
| 15 | 3.676665 | 0.5 | 1.882997 | 40.765107 |
| 16 | −9.095195 | 0.3749307 | | |
| 17 | 3.451026 | 0.25 | 1.846660 | 23.777940 |
| 18 | 1.273489 | 0.7 | 1.496999 | 81.545888 |
| 19 | ∞ | 0.03 | | |
| 20 | ∞ | 0.3 | 1.516330 | 64.142022 |
| 21 | ∞ | 1.840969 | | |
| 22 | ∞ | 0.4000947 | 1.516330 | 64.142022 |
| 23 | ∞ | 0.35 | 1.613500 | 50.200000 |
| Image pickup surface | ∞ | | | |

| Various data | |
|---|---|
| FL | 1.584 |
| L | 1.672 |
| Fno | 4.479 |
| ω | 60° |

| dome-shaped cover glass | |
|---|---|
| glass material | sapphire |
| outer diameter D | 5.4 |
| radius of curvature of an object-side surface R | 2.7 |
| thickness t | 0.3 |

Numerical values of the conditional expressions of each of examples are shown below.

| Conditional expression | | Example1 | Example2 | Example3 |
|---|---|---|---|---|
| (1) | L/FL | 1.029 | 1.056 | 0.9 |

| Conditional expression | | Example4 | Example5.6 | Example7 |
|---|---|---|---|---|
| (1) | L/FL | 1.4987 | 1.0276 | 1.0556 |

| Conditional expression | | Example5 | Example6 | Example7 |
|---|---|---|---|---|
| (2a) | t/D | 0.0315 | 0.1111 | 0.0556 |
| (2b) | t/(Fno × R) | 0.0138 | 0.0488 | 0.0248 |

As described above, according to the present invention it is possible to provide an endoscope objective optical system which enables to change a field of view to an arbitrary direction without bending an endoscope, even in a narrow space.

Various embodiments of the present invention have been described above. However, the present invention is not limited to these embodiments, and an embodiment in which the arrangements of these embodiments are combined appropriately without departing from the scope of the invention also fall under the category of the present invention.

As described above, the present invention is useful for an endoscope objective optical system to be used in a narrow space, and particularly is suitable for an endoscope objective optical system in which a field of view is let to be variable to an arbitrary direction.

The present invention shows an effect that it is possible to provide an endoscope objective optical system which enables to change a field of view to an arbitrary direction without bending an endoscope, even in a narrow space.

What is claimed is:

1. An endoscope objective optical system, comprising:
an optical-path deflecting prism group; and
a lens group, wherein
a visual-field direction of the endoscope objective optical system is let to be variable by moving a prism in the optical-path deflecting prism group, and
the optical-path deflecting prism group includes in order from an object side, three prisms namely, a first prism, a second prism, and a third prism, and the first prism, the second prism, and the third prism are disposed to be in mutual proximity, and the visual-field direction is let to be variable to a first direction by the first prism undergoing a rotational movement with respect to the second prism, and furthermore, the visual-field direction is let to be variable to a second direction which differs from the first direction, by the first prism and the second prism undergoing rotational movement integrally with respect to the third prism,
wherein the endoscope objective optical system satisfies the following conditional expression (1)

$$0.9 \leq L/FL \leq 1.5 \tag{1}$$

where,
L denotes a total air conversion length (unit mm) of the first prism, the second prism, and the third prism in the optical-path deflecting prism group, and here
the total air conversion length is a value obtained by summing up a value obtained by dividing a length of an optical axis passing through the first prism by a refractive index for a d-line nd1 of a glass material of the first prism, a value obtained by dividing a length of an optical axis passing through the second prism by a refractive index for the d-line nd2 of a glass material of the second prism, and a value obtained by dividing a length of an optical axis passing through the third prism by a refractive index for the d-line nd3 of a glass material of the third prism, and
FL denotes a focal length (unit mm) of the endoscope objective optical system.

2. The endoscope objective optical system according to claim 1, wherein
a dome-shaped cover glass is disposed between the endoscope objective optical system and an object, and
a thickness t of the dome-shaped cover glass satisfies the following conditional expression (2)

$$0.03 \times D \leq t \leq 0.05 \times Fno \times R \tag{2}$$

where,
D denotes an outer diameter (unit mm) of the dome-shaped cover glass,
t denotes the thickness (unit mm) of the dome-shaped cover glass,
Fno denotes an F-value of the endoscope objective optical system, and
R denotes a radius of curvature (unit mm) of an object-side surface of the dome-shaped cover glass, and moreover
when the outer diameter of the dome-shaped cover glass is not uniform, the largest portion is let to be the outer diameter (D), and when the thickness of the dome-shaped cover glass is not uniform, the thickest portion in an effective range is let to be the thickness (t).

3. The endoscope objective optical system according to claim 1, wherein
   a dome-shaped cover glass is disposed between the endoscope objective optical system and an object, and
   a center of curvature of an image-side surface of the dome-shaped cover glass is positioned on an axis of rotation when the first prism is made to undergo rotational movement with respect to the second prism, and is positioned on an axis of rotation when the first prism and the second prism are made to undergo rotational movement integrally with respect to the third prism.

* * * * *